US00PP12269P2

(12) United States Plant Patent

Lemon

(10) Patent No.: US PP12,269 P2
(45) Date of Patent: Dec. 11, 2001

(54) VARIETY OF GERANIUM PLANT NAMED 'REGAL BALLET'

(75) Inventor: David Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/715,311

(22) Filed: Nov. 17, 2000

(51) Int. Cl.[7] ..... A01H 5/00
(52) U.S. Cl. ..... Plt./331
(58) Field of Search ..... Plt./331

(56) References Cited

PUBLICATIONS

Gugenhan et al., Edelpelargonien Wieder Interessanter (A Renewed Interest in Pelargoniums), Deutscher Gartenbau vol. 31 (42), pp. 1712–1716; 1977 (Abstract).*

* cited by examiner

*Primary Examiner*—Bruce R. Campell
*Assistant Examiner*—Kent L. Bell
(74) *Attorney, Agent, or Firm*—Webb Ziesenheim Logsdon Orkin & Hanson, P.C.

(57) ABSTRACT

A new and distinct regal geranium plant with bright watermelon colored petals having deep burgundy eyes above medium green foliage.

1 Drawing Sheet

BACKGROUND OF THE INVENTION

The present invention comprises a new and distinct cultivar of *Pelargonium×domesticum* known by the varietal name 'Regal Ballet' (Oglevee No. 156, Breeder No. 5DG1925). The new variety was discovered in a selected breeding program in Lompoc, Calif. The new variety is a selection from the cross of 'Sandra', the female parent, (U.S. Plant Pat. No. 10,019) and an unpatented proprietary breeding variety (Oglevee No. 254), the male parent. The new variety was first asexually reproduced by cuttings at Oglevee, Ltd. in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 13 weeks from a rooted cutting to flowering in a 6 inch pot. The response time was determined on plants grown in soilless media employing constant fertilizer 150–200 parts per million of nitrogen and potassium in full light. Plants of 'Regal Ballet' differ from the plants of the parental cultivars primarily in flower color.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. The color readings were taken on a plant grown in a 6 inch pot indoors under 200–220 foot candles of fluorescent cool white light. Plants described were about 13 weeks old from a rooted cutting. Color references are primarily to The R.H.S. Colour Chart of The Royal Horticultural Society of London.

PLANT

Classification:
- *Botanical.*—*Pelargonium×domesticum.*
- *Commercial.*—Regal geranium.

Form: Medium mound.
Height: 21–23 cm from soil to top of foliage.
Growth: Upright, free basal branching.
Strength: Does not require artificial support.
Foliage: Stalked leaf attachment; medium green foliage.
Rooting time: Roots visible to outside of artificial dirt plug in 14–21 days.
Leaves:
- *Size.*—Length: 6–8.5 cm. Width: 9–10 cm.
- *Shape.*—Reniform; truncate base.
- *Margin.*—Serrated; slightly lobed.
- *Texture.*—Leathery; pubescent.
- *Color.*—Upper surface: Green Group 137C. Lower surface: Green Group 138B.
- *Ribs and veins.*—Venation: Palmate. Color: Yellow-Green Group 144C.

Petioles:
- *Color.*—Yellow-Green Group 144B.
- *Length.*—6.9–8.3 cm.

Stem:
- *Color.*—Yellow-Green Group 144A.
- *Internode length.*—1.5–3 cm.

THE BUD

Shape just prior to anthesis:
- *Overall.*—Elliptical cluster.
- *Individual bud.*—Elliptical.

Size when just showing color:
- *Overall.*—4.5–6.5 cm across.
- *Individual bud.*—1.9–2.3 cm long; 1–1.5 cm wide.

Number of buds per cluster: 7–15.

INFLORESCENCE

Blooming habit: Continuous; large flowers forming full flower heads.
- *Size.*—8.5–14.0 cm. across.
- *Borne.*—Flowers on umbel; umbel on pedicel; pedicel on peduncle.

Flowers:

*Form.*—Opened to slightly cupped; petals overlap; slightly ruffled.

*Number of flowers per umbel.*—5–8.

*Size.*—Diameter: 7.5–8.0 cm. Depth: 4.5–5.5 cm.

*Petals.*—Color: Upper surface: Lower Petals: Red Group 52C, fading to Red-Purple Group 58D toward base of petal, and white at petal base. A blotch of Greyed-Purple Group 187C is present in the center of the lower petals surrounded by a small area of Red Group 50A. Toward base of petal, this blotch fades to veining of Red-Purple Group 58A. Upper Petals: Outer edge Red-Purple Group 58C shading to Red Group 50A, Red-Purple Group 58D at lower outer edge of petal, and white at petal base. The upper petals are characterized by a large eye. The center of the eye is Greyed-Purple Group 187A fading toward the outer edge to Red Group 46A and then to Red Group 44A and then to Red Group 50A. Toward base of petal the Purple Group 187A shades to Red-Purple Group 61B. On older petals a silvery area appears over the top edge of the eye composed of small flecks of Grey Group 201C and 201D and Greyed-Purple Group 186D. Lower surface: Lower Petals: Outer edge Red Group 55B fading to Red Group 55C with blotch showing through. Upper Petals: Outer edge Red Group 55B, moving to Red Group 51A, and toward center of petal on edge, Red Group 50B with eye showing through. Shape: Obovate. Size: Length: 3.6–4.6 cm. Width: 4.5–5.2 cm. Margin: Entire. Number per flower: 5.

Texture and appearance: Smooth, velvety, highly reflective.

Tonality from a distance: Bright watermelon colored petals with dark eyes that have the appearance of deep burgundy velvet above medium green foliage.

Petaloids:

*Quantity.*—Some observed but not in every flower; 3–5 in number.

*Shape.*—Twisted; tubular; irregular.

*Color.*—Red Group 52C (both surfaces).

Pedicel:

*Length.*—2.8–3 cm.

*Color.*—Yellow-Green Group 144B.

Peduncle:

*Length.*—8–9 cm.

*Color.*—Yellow-Green Group 144A.

Disease/pest resistance: No susceptibility to diseases or pests has been noted to date.

Lasting quality: Individual umbels will last in the home environment for 4–6 weeks. Overall flowering will continue as long as conditions remain cool at night with plenty of light provided.

REPRODUCTIVE ORGANS

Stamens:

*Anthers.*—3–4 mm. in length.

*Filaments.*—Length: 1.7–2 cm. Color: White with pink-purple tips. Pollen: Golden orange.

Pistils:

*Number.*—One.

*Length.*—1.5–3 cm.

*Stigma.*—Number: One; five or six parted. Color: Greyed-Purple Group 187C.

*Style.*—Length: 12–14 mm. Color: Greyed-Purple Group 187C.

Ovaries:

*Completeness.*—Superior.

*Pubescence.*—Greatly pubescent.

*Length.*—5–8 mm.

*Width.*—3 mm.

*Color.*—Yellow-Green Group 145D.

Fruit: None observed.

GENERAL CHARACTERISTICS

1. The flower color of 'Regal Ballet' is a new and unique color in the Elegance Series.

2. Cutting production and rooting speed are comparable to 'Fantasy', (U.S. Plant Pat. No. 7,538).

3. Very large flower size with slight ruffling.

4. Plant habit is controlled and forms a mound shape.

I claim:

1. A new and distinct variety of geranium plant substantially as shown and described.

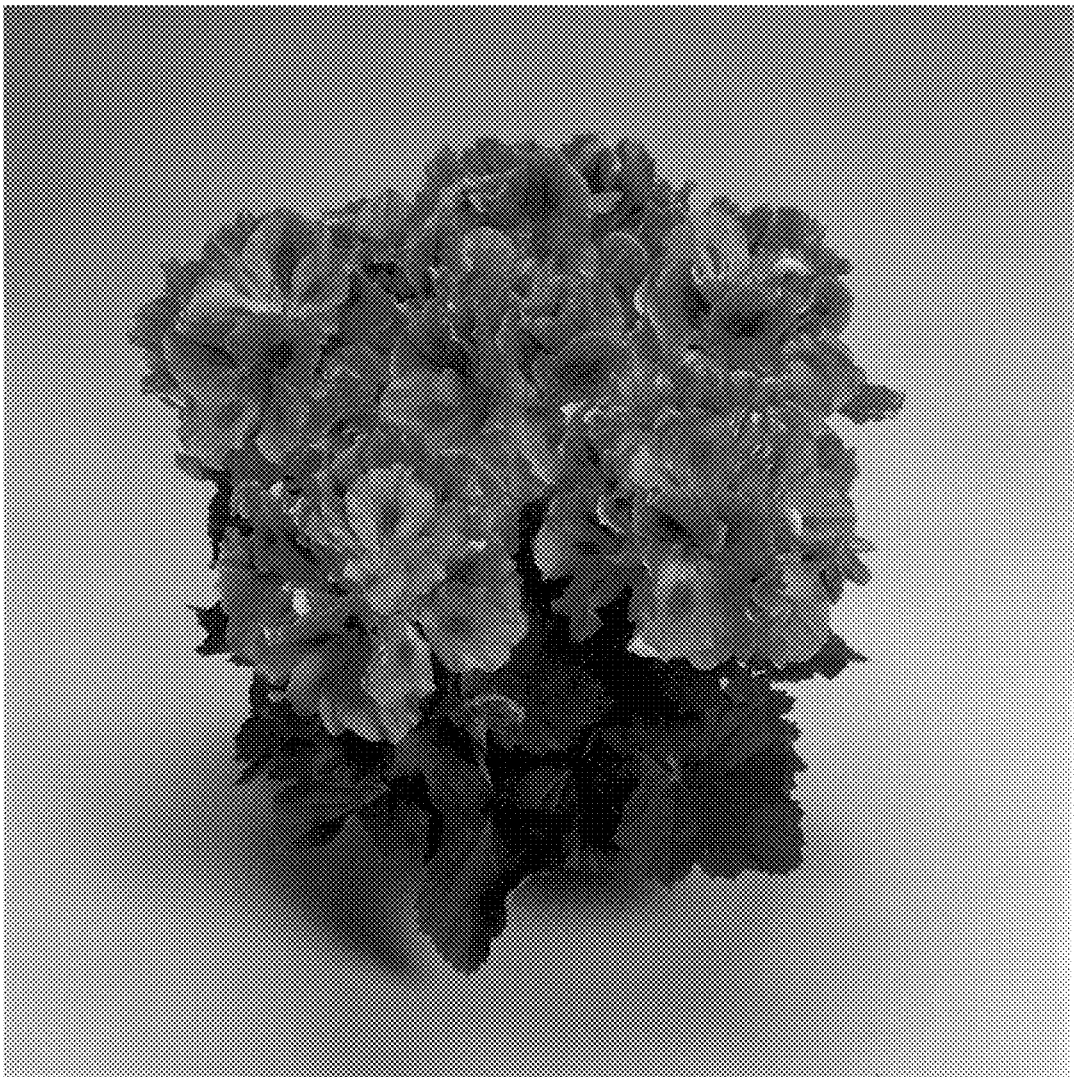

* * * * *